United States Patent [19]
Weiser

[11] Patent Number: 6,149,901
[45] Date of Patent: Nov. 21, 2000

[54] ANIMAL SCENT ENHANCER

[75] Inventor: Mark J. Weiser, Evans City, Pa.

[73] Assignee: EBSCO Industries, Inc., Birmingham, Ala.

[21] Appl. No.: 09/376,110

[22] Filed: Aug. 17, 1999

[51] Int. Cl.⁷ .......................... A01N 59/06; A01N 59/08; A01N 59/00; A01N 63/00; A01N 25/08

[52] U.S. Cl. .......................... 424/84; 424/409; 424/417; 424/520; 424/522; 424/523; 424/543; 424/545; 424/546; 424/682; 424/686; 424/687; 424/715; 424/722; 424/724

[58] Field of Search .............................. 424/84, 682, 686, 424/687, 715, 722, 724, 523, 543, 545, 409, 417, 520, 522, 546

[56] References Cited

U.S. PATENT DOCUMENTS

| | | | |
|---|---|---|---|
| 5,292,495 | 3/1994 | Nakajima et al. | 423/432 |
| 5,672,342 | 9/1997 | Bell | 417/84 |

OTHER PUBLICATIONS

Chemical Abstracts 90: 142087, 1979.

*Primary Examiner*—John Pak
*Attorney, Agent, or Firm*—Burr & Forman, LLP; Robert J. Veal; Christopher A. Holland

[57] ABSTRACT

The present invention relates to animal scent attractants. More particularly, the present invention relates to a composition of matter for amplifying and preserving animal scents. Fox urine, coyote urine, deer urine, elk urine, moose urine, bear urine, rabbit urine, fish oils, and sheep manure are examples of substances which can be used with the present invention.

15 Claims, No Drawings

ANIMAL SCENT ENHANCER

FIELD OF THE INVENTION

The present invention relates to scents used to attract animals. More particularly, the present invention relates to a composition of matter for amplifying and preserving animal scents, such as animal urine.

BACKGROUND OF THE INVENTION

Animal scents have been used by hunters and wildlife enthusiasts for a number of different purposes. A primary reason animal scents are used is to attract animals to a desired area. Pursuant to the same objective, animal scents are also used to disguise or mask human scent. Animals possess a keen sense of smell which can detect human scent from great distances and consequently keep the animals from the area in which the human is located.

Examples of animal scents are taught in U.S. Pat. No. 4,944,940 to Christenson, II and U.S. Pat. No. 5,672,342 to Bell. Christenson, II teaches animals scents wherein urine from a number of different animals are blended together, and Bell teaches a method of making an animal scent kit with urine from a single animal.

There are several problems associated with prior art animal scents. First, none of the prior art compositions or methods provide adequate means to enhance the scent such that the scent will reach animals which are at a significant distance from the source. Thus, outdoorsmen are faced with the choice of placing large quantities of animal scents in the desired area or risking animals detecting their human scent.

Additionally, the scent of animal urine fades, leaving human scent exposed. One popular method of masking human scent is accomplished primarily by applying animal urine to a drag line attached to the person and allowing it to contact the ground, leaving a trail of animal scent. However, liquid animal scents used in this method often dissipate quickly. Further, large quantities of urine are often wasted in an attempt to apply urine to a drag line.

Another problem associated with the prior art is the cumbersome task of carrying around large quantities of animal urine. It is often inconvenient for one using animal urine as a scent to carry large quantities of urine in light of other needed equipment such as guns, food, drinking water, and camera equipment. In other words, large quantities of liquid animal scents can consume too much of the limited amount of space available to outdoorsmen.

Moreover, extreme weather temperatures also present problems for liquid animal scents. Liquid animal scents can evaporate under high temperatures, requiring continual replenishment of the liquid animal scents in the desired area. On the other hand, liquid animal scents can also freeze during cold temperatures further thwarting the ability of the liquid animal scents to emit an odor sufficient to reach animals at even marginal distances.

What is needed is a composition of matter for amplifying and preserving animal scents which overcomes the problems found with prior art animal scents.

SUMMARY OF THE INVENTION

The present invention comprises a composition of matter for preserving and amplifying liquid animal scents consisting essentially of calcium carbonate and liquid animal scent. Fox urine, coyote urine, deer urine, elk urine, moose urine, bear urine, rabbit urine, and fish oils are examples of liquid animal scents which can be used with the present invention.

In an alternate embodiment for preserving and amplifying freeze dried animal scents, the composition consists essentially of calcium carbonate and freeze dried animal scent. Fox urine, coyote urine, deer urine, elk urine, moose urine, bear urine, rabbit urine, fish oils, and sheep manure are examples of substances which can be dried and used with the present invention.

The present invention is a powder which enhances the scent emitted by animal scents by amplifying the scent and thereby substantially increasing the coverage area thereof. The present invention's increased range and strength also reduce the amount of scent which is necessary to be used and carried on trips. Further, because the present invention is a powder, the invention eliminates the potential of spilling urine or breaking containers of liquid animal scents. Moreover, using powdered animal scent further reduces the quantity of animal scent needed for a trip, and eliminates the problem associated with pouring liquid animal scents onto a drag line. Finally, the powdered form of the present invention eliminates the problem associated with extreme temperatures.

These and other objects and advantages of the invention will become apparent from the following detailed description of the preferred embodiment of the invention.

DETAILED DESCRIPTION OF THE PREFERRED EMBODIMENTS

While the present invention is satisfied by embodiments in a range of compositions, there will be described herein examples of the preferred embodiments of the invention, with the understanding that the present disclosure is to be considered as exemplary of the principles of the invention and is not intended to limit the invention to the embodiments described.

With the foregoing in mind, the composition of matter of the present invention is a powder comprising calcium carbonate and animal scent wherein the animal scent is preferably selected from the group consisting of liquid and freeze dried animal urine. The calcium carbonate is present in the composition between about 80–99%, most preferably between 85–95%, and the animal scent is present in the composition between about 1–20%, most preferably between about 5–10%. A percentage of animal scent below 1% results in a composition having an undesirable scent potency and a percentage of animal scent above 20% results in clumping of the powder.

The composition of matter of the present invention preferable for preserving and amplifying liquid animal scents consists essentially of between about 85–95% by weight of calcium carbonate, between about 1–2% by weight of magnesium carbonate, between about 0–7% by weight of sodium chloride, about 0.8% by weight of crystalline silica, and between about 5–10% by weight of liquid animal scent. The magnesium carbonate, sodium chloride, and crystalline silica are not critical to the composition of the present invention. Fox urine, coyote urine, deer urine, elk urine, moose urine, bear urine, rabbit urine, and fish oils are examples of liquid animal scents which can be used with the present invention.

The composition preferable for preserving and amplifying freeze dried animal scents consists essentially of between about 85–95% by weight of calcium carbonate, between about 1–2% by weight of magnesium carbonate, about 0.8% of crystalline silica, and between about 5–10% by weight of a freeze dried animal scent. The magnesium carbonate and crystalline silica are not critical to the composition of the present invention. Fox urine, coyote urine, deer urine, elk urine, moose urine, bear urine, rabbit urine, fish oils, and sheep manure are examples of animal scents which can be dried and used with the present invention.

In an alternate embodiment, the composition preferable for preserving and amplifying either liquid or freeze dried animal scents consists essentially of between about 85–95% by weight of calcium carbonate, between about 7–9% by weight of magnesium carbonate, about 0.8% of crystalline silica, and between about 5–10% by weight of animal scent. Again, the magnesium carbonate and crystalline silica are not critical to the composition of the present invention.

The present invention will hereinafter be described more specifically by the following examples. All designations of "%" used in the following examples mean percent (%) by weight unless expressly noted.

The following are examples of compositions for preserving and amplifying liquid animal scents:

EXAMPLE 1

86.2% of calcium carbonate,
1% of magnesium carbonate,
7% of sodium chloride,
0.8% of crystalline silica, and
5% of animal urine.

EXAMPLE 2

86.2% of calcium carbonate,
1% of magnesium carbonate,
6% of sodium chloride,
0.8% of crystalline silica, and
6% of animal urine.

EXAMPLE 3

92% of calcium carbonate, and
8% of animal urine.

The following are examples of compositions for preserving and amplifying a freeze dried animal scent:

EXAMPLE 4

92.2% of calcium carbonate,
1% of magnesium carbonate,
0.8% of crystalline silica, and
6% of freeze dried animal urine.

EXAMPLE 5

90.2% of calcium carbonate,
1% of magnesium carbonate,
0.8% of crystalline silica, and
8% of freeze dried animal urine.

EXAMPLE 6

92% of calcium carbonate, and
8% of freeze dried animal urine.

It is to be understood that the forms of the invention described are preferred embodiments thereof and that various changes and modifications may be made therein without departing from the spirit of the invention or scope as defined in the following claims.

Having set forth the nature of the invention, what is claimed is:

1. A composition of matter for amplifying animal scents, consisting essentially of:
   (a) calcium carbonate, wherein said calcium carbonate is present in said composition in an amount between about 80–99% by weight,
   (b) magnesium carbonate,
   (c) crystalline silica, and
   (d) liquid animal scent.

2. A composition of matter according to claim 1, wherein said calcium carbonate is present in said composition in an amount between about 85–95% by weight.

3. A composition of matter according to claim 1, wherein said magnesium carbonate is present in said composition in an amount between about 1–2% by weight.

4. A composition of matter according to claim 1, wherein said magnesium carbonate is present in said composition in an amount between about 7–9% by weight.

5. A composition of matter according to claim 1, wherein said crystalline silica is present in said composition in an amount of about 0.8% by weight.

6. A composition of matter according to claim 1, wherein said liquid animal scent is present in said composition in an amount between about 5–10% by weight.

7. A composition of matter according to claim 1, further comprising sodium chloride, wherein said sodium chloride is present in said composition in an amount between about 0.5–7% by weight.

8. A composition of matter according to claim 1, wherein said animal scent is selected from the group consisting of fox urine, coyote urine, deer urine, elk urine, moose urine, bear urine, rabbit urine, and fish oil.

9. A composition of matter for amplifying animal scents, consisting essentially of:
   (a) calcium carbonate, wherein said calcium carbonate is in said composition in an amount between about 80–99% by weight,
   (b) crystalline silica,
   (c) magnesium carbonate, and
   (d) Freeze-dried animal scent.

10. The composition of matter according to claim 9, wherein said calcium carbonate is in said composition in an amount between about 85–95% by weight.

11. A composition of matter according to claim 9, wherein said crystalline silica is in said composition of matter in an amount of about 0.8% by weight.

12. A composition of matter according to claim 9, wherein said magnesium carbonate is in said composition of matter in an amount between about 1–2% by weight.

13. A composition of matter according to claim 9, wherein said magnesium carbonate is in said composition of matter in an amount between about 7–9% by weight.

14. A composition of matter according to claim 9, wherein said animal scent is in said composition in an amount between about 5–10% by weight.

15. A composition of matter according to claim 9, wherein said animal scent is selected from the group consisting of freeze dried fox urine, freeze dried deer urine, freeze dried elk urine, freeze dried moose urine, freeze dried bear urine, freeze dried rabbit urine, freeze dried fish oil, and freeze dried sheep manure.

\* \* \* \* \*